United States Patent [19]
Winters et al.

[11] Patent Number: 5,342,693
[45] Date of Patent: Aug. 30, 1994

[54] MULTIFUNCTIONAL THROMBO-RESISTANT COATING AND METHODS OF MANUFACTURE

[75] Inventors: Suzanne Winters, Salt Lake City; Kenneth A. Solen, Orem; Clifton G. Sanders, Salt Lake City; J. D. Mortensen, Sandy; Gaylord Berry, Salt Lake City, all of Utah

[73] Assignee: Cardiopulmonics, Inc., Salt Lake City, Utah

[21] Appl. No.: 35,426

[22] Filed: Mar. 22, 1993

Related U.S. Application Data

[60] Continuation of Ser. No. 823,271, Jan. 21, 1992, abandoned, which is a division of Ser. No. 215,014, Jul. 5, 1988, Pat. No. 5,262,451, which is a continuation-in-part of Ser. No. 204,115, Jun. 8, 1988, Pat. No. 4,850,958.

[51] Int. Cl.$^5$ .................... B32B 27/06; A01N 1/00
[52] U.S. Cl. .................... 428/447; 428/451; 523/112; 530/812; 530/815; 530/816
[58] Field of Search .......... 523/112; 424/78.27; 530/812, 815, 816; 428/447, 451; 604/265, 266

[56] References Cited

U.S. PATENT DOCUMENTS

| | | | |
|---|---|---|---|
| 3,279,996 | 10/1966 | Long, Jr. et al. | 167/82 |
| 3,453,194 | 7/1969 | Bennett et al. | 204/159.12 |
| 3,522,346 | 7/1970 | Chang | 424/35 |
| 3,639,141 | 2/1972 | Dyck | 117/47 A |
| 3,673,612 | 7/1972 | Merrill et al. | 3/1 |
| 3,759,788 | 9/1973 | Gajewski et al. | 195/1.8 |
| 3,810,781 | 5/1974 | Eriksson et al. | 117/47 A |
| 3,826,678 | 7/1974 | Hoffman | 117/81 |
| 3,846,353 | 11/1974 | Grotta | 260/9 |
| 3,865,615 | 2/1975 | Manly | 117/47 A |
| 3,888,833 | 6/1975 | Lednicer et al. | 260/79.3 R |
| 3,940,506 | 2/1976 | Heinecke | 427/38 |
| 3,959,128 | 5/1976 | Harris | 210/24 |
| 3,969,240 | 7/1976 | Kolobow et al. | 210/22 |
| 3,992,495 | 11/1976 | Sano et al. | 264/22 |
| 4,008,047 | 2/1977 | Petersen | 23/258.5 |
| 4,059,512 | 11/1977 | Harris | 210/24 |

(List continued on next page.)

FOREIGN PATENT DOCUMENTS

| | | | |
|---|---|---|---|
| 0054919 | 12/1980 | European Pat. Off. | A61L 17/00 |
| 0152699 | 8/1985 | European Pat. Off. | A61L 33/00 |
| 263184A1 | 4/1988 | European Pat. Off. | A61M 1/18 |
| 0263184 | 4/1988 | European Pat. Off. | G01N 33/545 |

(List continued on next page.)

OTHER PUBLICATIONS

Bell, A. T. et al., "A Study of the Performance and Chemical Characteristics of Composite Reverse Osmosis Membranes Prepared by Plasma Polymerization of Allylamine," *Journal of Applied Polymer Science*, vol. 19, pp. 1911-1930 (1975).

Buijten, J. et al., "Immobilization of Polyethylene Glycon in Capillary Columns for Gas Chromatography," *J. Chromat.*, 268, pp. 387-394 (1983).

Chawla, Attar S., "Use of Plasma Polymerization for Preparing Silicone-Coated Membranes for Possible Use (List continued on next page.)

*Primary Examiner*—Peter Szekely
*Attorney, Agent, or Firm*—Workman Nydegger Jensen

[57] ABSTRACT

The present invention is directed to multifunctional thrombo-resistant coatings for use with biomedical devices and implants, such as a coating which includes a siloxane surface onto which a plurality of amine functional groups have been bonded. Covalently bonded to the amine functional groups are a plurality of poly(ethylene oxide) chains, such that a single poly(ethylene oxide) chain is bonded to a single amine functional group. A plurality of different bioactive molecules, designed to counteract specific blood-material incompatibility reactions, are covalently bonded to poly(ethylene oxide) chains, such that a single bioactive molecule is coupled to a single polyethylene oxide chain.

The methods of manufacturing the present invention include preparing a material having a siloxane surface onto which a plurality of amine functional groups have been bonded. This is achieved by plasma etching with ammonia gas or by plasma polymerization of a siloxane monomer in the presence of ammonia gas. The amine-containing siloxane surface is reacted with poly(ethylene oxide) chains terminated with functional groups capable of reacting with the amine groups on the siloxane surface. The material is then reacted with a plurality of different bioactive molecules which counteract the specific blood-material incompatibility reactions, such that a single bioactive molecule is coupled to a single poly(ethylene oxide) chain. The resulting siloxane surface contains a plurality of different bioactive molecules capable of reacting with blood components which come in proximity to the siloxane surface in order to resist blood-material incompatibility reactions.

6 Claims, No Drawings

U.S. PATENT DOCUMENTS

| | | | |
|---|---|---|---|
| 4,061,141 | 12/1977 | Hyden et al. | 128/214 |
| 4,093,515 | 6/1978 | Kolobow et al. | 195/1.8 |
| 4,170,559 | 10/1979 | Kroplinski et al. | 210/321 |
| 4,210,529 | 7/1980 | Petersen | 210/22 |
| 4,213,962 | 7/1980 | Miura et al. | 424/78.27 |
| 4,214,020 | 7/1980 | Ward et al. | 427/296 |
| 4,243,776 | 1/1981 | Marconi et al. | 525/420 |
| 4,329,383 | 5/1982 | Joh | 428/36 |
| 4,331,697 | 5/1982 | Kudo et al. | 427/2 |
| 4,349,467 | 9/1982 | Williams et al. | 525/54.2 |
| 4,378,803 | 4/1983 | Takagi et al. | 604/280 |
| 4,410,338 | 10/1983 | Yamamoto et al. | 55/158 |
| 4,444,662 | 4/1984 | Conover | 210/500 |
| 4,483,901 | 11/1984 | Okita et al. | 428/315.5 |
| 4,500,676 | 2/1985 | Balazs | 525/54.2 |
| 4,521,564 | 6/1985 | Solomon et al. | 525/54.1 |
| 4,600,652 | 7/1986 | Solomon et al. | 428/423.3 |
| 4,613,517 | 9/1986 | Williams et al. | 427/2 |
| 4,613,665 | 9/1986 | Larm | 536/20 |
| 4,622,206 | 11/1986 | Torgeson | 422/48 |
| 4,666,668 | 5/1987 | Lidorenko et al. | 422/48 |
| 4,673,584 | 6/1987 | Nygren et al. | 427/2 |
| 4,686,975 | 8/1987 | Naimon et al. | 128/204 |
| 4,770,852 | 9/1988 | Takahara et al. | 422/48 |
| 4,781,889 | 11/1988 | Fukasawa et al. | 422/48 |
| 4,806,246 | 2/1989 | Nomura | 210/651 |
| 4,806,595 | 2/1989 | Noishiki et al. | 525/54.2 |
| 4,810,784 | 3/1989 | Larm | 536/20 |
| 4,822,741 | 4/1989 | Banes | 435/300 |
| 4,824,444 | 4/1989 | Nomura | 15/16 |
| 4,828,561 | 5/1989 | Woodroof | 623/8 |
| 4,844,986 | 7/1989 | Karakelle et al. | 428/447 |
| 4,846,844 | 7/1989 | De Leon et al. | 623/66 |
| 4,861,830 | 8/1989 | Ward, Jr. | 525/92 |
| 4,872,867 | 10/1989 | Joh | 604/269 |
| 4,879,135 | 11/1989 | Greco et al. | 427/2 |
| 4,919,659 | 4/1990 | Horbett et al. | 623/1 |
| 5,004,461 | 4/1991 | Wilson | 604/265 |
| 5,013,717 | 5/1991 | Solomon et al. | 514/56 |
| 5,019,393 | 5/1991 | Ito | 424/423 |
| 5,026,607 | 6/1991 | Kiezulas | 428/423.7 |
| 5,053,048 | 10/1991 | Pinchuk | 623/1 |
| 5,053,453 | 10/1991 | Ku | 525/54.1 |
| 5,061,738 | 10/1991 | Solomon et al. | 523/100 |

FOREIGN PATENT DOCUMENTS

| | | | |
|---|---|---|---|
| 0332261 | 9/1989 | European Pat. Off. | A61L 33/00 |
| 0335972 | 10/1989 | European Pat. Off. | A61L 33/00 |
| 0351314 | 1/1990 | European Pat. Off. | A61L 33/00 |
| 0354061 | 2/1990 | European Pat. Off. | A61M 1/34 |
| 0357242 | 3/1990 | European Pat. Off. | A61L 33/00 |
| 0404683 | 12/1990 | European Pat. Off. | A61L 33/00 |
| WO91/12886 | 9/1991 | European Pat. Off. | B01D 15/08 |
| 135495 | 10/1979 | Japan | A61M 1/03 |
| 1391028 | 4/1975 | PCT Int'l Appl. | C07G 7/00 |
| WO88/02623 | 4/1988 | PCT Int'l Appl. | A61F 2/54 |
| WO90/01305 | 2/1990 | PCT Int'l Appl. | A61F 2/02 |
| WO91/16932 | 11/1991 | PCT Int'l Appl. | A61L 33/00 |
| 2001663 | 2/1979 | United Kingdom | C08G 69/48 |
| 2167665A | 6/1988 | United Kingdom | A61F 2/00 |

OTHER PUBLICATIONS in Blood Oxygenators," *Artificial Organs*, vol. 3, No. 1, pp. 92–96 (Feb. 1979).

Chung-Peng, Ho et al., "Modification of Silicone Contact Lenses by Plasma Plasma Polymerization and Subsequent Plasma Treatments," University of Missouri-Rolla, pp. 705–709 (undated).

Denaro, A. R. et al., "Glow Discharge Polymerization—III Allyl Alcohol and Crotyl Alcohol," *Euro. Poly. J.*, vol. 6, pp. 487–497 (1970).

Doblhofer, K. et al., "Electrochemical Performance of Fixed-Charge Polymer Films Prepared on Electrodes by Plasma Polymerization," *Thin Solid Films*, vol. 118, pp. 181–185 (1984).

Elam, E. H. et al., "Covalent Coupling of Polysaccarides to Silicon and Silicon Rubber Surfaces," *J. Biomed. Mater. Res.*, vol. 18, pp. 953–959 (1984).

Gombotz, Wayne et al., "Immobilized Enzymes in Blood Plasma Exchanges via Radiation Grafting," *Radiat. Phys. Chem.*, vol. 25, Nos. 4–6, pp. 549–556 (1985).

Gombotz, W. R. et al., "Functionalization of Polymeric Films by Plasma Polymerization of Allyl Alcohol and Allylamine," *ACS Symposium Abstracts*, vol. 56 (1987).

Gregonis, D. E. et al., "Poly(Ethylene Glycol) Surfaces to Minimize Protein Absorption," Second World Congress on Biomaterials Abstracts, 10th Annual Meeting of the Society of Biomaterials, Wash., D.C. (1984).

Hoffman, Allan S., "Blood–Biomaterial Interactions: An Overview," *American Chemical Society*, pp. 3–8 (1982).

Hollahan, J. R. et al., "Attachment of Amino Groups to Polymer Surfaces by Radio-frequency Plasmas," *J. Appl. Poly. Sci.*, 13, pp. 807–816 (1969).

Hollahan, J. R. et al., "Hydroxylation of Polymethal Siloxane Surfaces by Oxidizing Plasmas," *J. Appl. Poly. Sci.* 14, pp. 2499–2508 (1970).

Jacobs, H. A., "PGEI-Heparin Conjugate: Synthesis, Characterization and Application," Dissertation submitted to the University of Utah (1987).

Kaetsu, Isao et al., "Studies on the Immobilization of Biofunctional Components by Radiation Polymerization and their Applications", *Radia Phys. Chem.*, 27 vol. 27, pp. 245–263 (1986).

Ketteringham, John M. et al., "Permeable Surfaces," *Annals New York Academy of Sciences*, vol. 283, pp. 410–418 (1977).

Ketteringham, J. et al., "A High Permeability, Nonporous, Blood Compatible Membrane for Membrane Lungs: In Vivo and In Vitro Performance," *Trans. Amer. Soc. Artif. Int. Organs*, vol. XXI, pp. 224–233 (1975).

Kim, S. W. et al., "Nonthrombogenic Bioactive Surfaces," from *Annals of the New York Academy of Sci-*

(List continued on next page.)

OTHER PUBLICATIONS

*ences,* vol. 516, pp. 116–130 (undated).

Kuzuya, Masayuki et al., "Mechanistic Insight into Immobilization and Release of Active Radical Species on a Novel Plasma–Driven Ultrathin Film," *Chemistry Letters* (one page), (1986).

Mori, Y. et al., "Permeability of Heparinized Hydrophilic Polymer (H–RSD): Application to Semipermeable Membrane for Microencapsulation of Activated Charcoal," *J. Biomed. Mater. Res.,* vol. 16, pp. 17–30 (1982).

Pekala, Richard W. et al., "XPS Determination of Molecular Rearrangement at the Surface of a Cross-linked Polymer System," *Journal of Colloid and Interface Science,* vol. 101, No. 1, pp. 121–128 (Sep. 1984).

Pekala, R. W. et al., "Cross-linked Polyether/Polysiloxane Networks for Blood-Interfacing Applications," *Biomaterials,* vol. 7, pp. 372–378 (Sep. 1986).

Pekala, R. W. et al., "Fibrinogen Absorption and Platelet Adhesion at the Surface of Modified Polypropylene Glycol/Polysiloxane Networks," *Biomaterials,* vol. 7, pp. 379–385 (Sep. 1986).

Peric, D. et al., "Reverse Osmosis Characteristics of Composite Membranes Prepared by Plasma Polymerization of Allylamine. Effects of Deposition Conditions," *J. Appl. Poly. Sci.,* vol. 21, pp. 2661–2673 (1977)

Ruckenstien, E. et al., "Preparation and Characterization of Thin Film Surface Coatings for Biological Environments," *Biomaterials,* vol. 7, pp. 403–422 (Nov 1986).

Sadhir, R. K. et al., "Deposition and Characterization of Plasma Polymerized Films of Hexafluorobenzene and Ammonia," *ACS Symposium Abstracts,* 56 (1987).

Sharma, A. K. et al., "Plasma Polymerization of Tetramethyldisiloxane by a Magnetron Glow Discharge," *Thin Solid Films,* vol. 110, pp. 171–184 (1983).

Sipehia, R. et al., "Albuminated Polymer Surfaces for Biomedical Application," *Biomat. Med. Dev. Art. Org.,* vol. 10, No. 4, pp. 229–246 (1982).

Sepehia, R. et al., "Enhanced Albumin Binding to Polypropylene Beads Via Anhydrous Ammonia Gaseous Plasma," *Biomater.,* vol. 7, pp. 471–473 (1986).

Sowell, R. R. et al., "Effect of Activated Gas Plasma on Surface Characteristics and Bondability of RTV Silicone and Polyethylene," *J. Adhesion,* No. 4, pp. 15–24 (1972).

Winters, S. et al., "Absorption of Antithrombin III," Second World Congress on Biomaterials, Abstracts 10th Annual Meeting of the Society for Biomaterials, Wash., D.C. (Apr. 27–May 1, 1984).

Winters, S. "Immobilized Heparin via a Long Chain Poly(ethyleneoxide) Spacer for Protein and Platelet Compatibility," Dissertation submitted to Department of Pharmaceutics, University of Utah (1987).

Yasuda, H., "Modification of Polymers of Plasma Treatment and by Plasma Polymerization," *Radiat. Phys. Chem.,* vol. 9, pp. 805–817 (1977).

Yeh, Y. S., et al., "Blood Compatibility of Plasma Polymers," Graduate Center for Materials Reserach Center, University of Missouri–Rolla, pp. 715–719.

MULTIFUNCTIONAL THROMBO-RESISTANT COATING AND METHODS OF MANUFACTURE

THE RELATED APPLICATIONS

This application is a file wrapper continuation of U.S. application Ser. No. 07/823,271, filed Jan. 21, 1992, for MULTIFUNCTIONAL THROMBO-RESISTANT COATINGS AND METHODS OF MANUFACTURE which is now abandoned which is a divisional of application Ser. No. 07/215,014, filed Jul. 5, 1988, now U.S. Pat. No. 5,262,451, which is a continuation-in-part of copending application Ser. No. 07/204,115, filed Jun. 8, 1988, now U.S. Pat. No. 4,850,958, in the name of Gaylord Berry, J. D. Mortensen, and Larry D. Rigby and entitled "Apparatus and Method for In Vivo Extrapulmonary Blood Gas Exchange."

BACKGROUND

1. The Field of the Invention

The invention relates to thrombo-resistant compositions for coating polymers and to the methods of manufacturing such coatings. More particularly, the present invention immobilizes on the surface of a gas permeable polymer, a wide range of bioactive substances which combat the various blood-material incompatibility reactions.

2. The Prior Art

Over the years, a large number of medical devices have been developed which contact blood. The degree of blood contact varies with the device and its use in the body. For instance, catheters may briefly contact the blood, while implants, such as heart valves and vascular grafts, may contact blood for a number of years. Regardless of the device, blood contact with foreign materials initiates the process of thrombosis, often followed by formation of thromboemboli.

Adsorption of proteins is one of the first events to occur when blood contacts a foreign surface. The compositions and conformation of adsorbed proteins influence subsequent cellular responses such as platelet adhesion, aggregation, secretion, complement activation, and ultimately, the formation of cross-linked fibrin and thrombus. Thrombus formation is by far the most obvious and potentially debilitating response to foreign material in contact with blood.

The initial protein layer at the blood-material II interface is subject to denaturation, replacement, and further reaction with blood components. During this phase of protein adsorption, adsorbed fibrinogen is converted to fibrin. Fibrin formation is accompanied by the adherence of platelets and possibly leucocytes. The platelets become activated and release the contents of their granules. This activates other platelets, thereby resulting in platelet aggregation.

A thrombus eventually forms from entrapment of erythrocytes (red blood cells) and other blood constituents in the growing fibrin network. Thrombus growth can eventually lead to partial or even total blockage of the device unless the thrombus is sheared off or otherwise released from the foreign surface as an embolus. Unfortunately, such emboli can be as dangerous as blockage of the device since emboli can travel through the bloodstream, lodge in vital organs, and cause infarction of tissues. Infarction of the heart, lungs, or brain, for example, can be fatal. Therefore, the degree to which the foreign material inhibits thrombus formation, embolization, and protein denaturation determines its usefulness as a biomaterial.

In the past, the thrombogenicity of biomedical implants has been treated by the administration of systemic anticoagulants, e.g., heparin and warlatin. However, long-term anticoagulation therapy is not advisable due to the risk of hazardous side effects. Moreover, overdose of anticoagulants may cause lethal side reactions, such as visceral or cerebral bleeding. For these reasons, there have been extensive efforts to develop materials which can be used in biomedical devices or implants which can contact blood with minimal or no systemic anticoagulation therapy being necessary to avoid thrombus formation.

Many studies have attempted to produce a nonthrombogenic blood-contacting surface through immobilization of biologically active molecules onto the surface. Such bioactive molecules counteract various blood-material incompatibility reactions.

Surface modification of polymeric materials offers the advantage of optimizing the chemical nature of the blood/polymer interface while allowing a choice of the substrate to be based upon the necessary mechanical properties of the blood-contacting device.

The methods used to immobilize bioactive molecules onto blood-contacting surfaces fall into four general groups: physical adsorption, physical entrapment, electrostatic attraction, and covalent binding.

Surfaces incorporating bioactive molecules by physical adsorption or entrapment beneath the blood-contacting surface exhibit a significant degree of thrombo-resistance. However, depletion of the bioactive molecules into the blood environment causes the surface to rapidly lose its thrombo-resistant character. Entrained molecules diffuse to the surface which, along with physically adsorbed bioactives, are then "leached" from the surface into the blood plasma by mechanical and chemical mechanisms.

Similarly, electrostatically or ionically bound molecules are subject to partitioning and ion exchange between the blood-contacting surface and the electrolyte-rich plasma resulting in depletion. Covalently bound bioactive molecules resist depletion sufficiently to offer a potentially "long term" thrombo-resistant effect.

Numerous studies of covalent attachment of different biomolecules are available. These studies generally involve the covalent attachment of a single bioactive molecule, usually heparin, designed to counteract one aspect of the blood-material incompatibility reactions. Most studies have focused on covalently binding heparin to a blood-contacting surface. Heparin is the most frequently prescribed anticoagulant in use today. It is a highly sulfonated mucopolysaccharide containing a number of charged functional groups. Heparin enhances the inactivation of thrombin by antithrombin III, thereby inhibiting the conversion of fibrinogen to fibrin.

Most prior attempts to covalently bind heparin to a blood-contacting surface have severely decreased the activity of heparin. For example, heparin coupled to a blood-contacting surface through one of its carboxyl groups loses up to 90% of its activity. Other systems, claiming covalent attachment of heparin, are actually heparin covalently bound to a coupling molecule which subsequently ionically bound to the substrate.

Additional problems are encountered when the blood-contacting surface must also be gas permeable. Siloxane polymers are of particular interest in blood gas exchange devices because siloxane polymers not only possess certain inherent thrombo-resistant properties, but siloxane polymers also are gas permeable. However, siloxane polymers are relatively inert and pose a significant obstacle in modifying the surface in order to become more thrombo-resistant.

From the foregoing, it will be appreciated that what is needed in the art are multifunctional thrombo-resistant compositions and methods which counteract a wide range of blood material incompatibility reactions.

Additionally, it would be a significant advancement in the art to provide multifunctional thrombo-resistant compositions and methods which do not inhibit the gas permeability of the blood-contacting surface.

It would be another advancement in the art to provide multifunctional thrombo-resistant compositions and methods in which the bioactive molecules are covalently bound to the blood-contacting surface, thereby eliminating elution of the bioactive molecules into the blood plasma.

It would be a further advancement in the art to provide multifunctional thrombo-resistant compositions and methods in which the bioactive molecules retain their activity after immobilization on the blood-contacting surface.

The foregoing, and other features and objects of the present invention, are realized in the multifunctional thrombo-resistant compositions and methods which are disclosed and claimed herein.

BRIEF SUMMARY AND OBJECTS OF THE INVENTION

The present invention is directed to multifunctional thrombo-resistant coatings for use with biomedical devices and implants. A variety of bioactive molecules which individually counteract specific blood-material incompatibility reactions are immobilized onto the polymeric surface of the device which is to contact the blood.

Siloxane is the presently preferred substrate surface (that is, to which the multiple bioactive moleculars are bonded), because the substrate itself is initially relatively thrombo-resistant. Moreover, siloxane is gas permeable, thereby broadening the applications for the coatings of the present invention. Nevertheless, it will be appreciated from the specifications set forth below that other substrates are within the scope of the present invention.

In order to overcome the inertness of the siloxane surface, functional groups, preferably amine groups, are introduced onto the siloxane surface. Two methods are currently preferred to introduce amine functionalities to the polymeric surface: (1) plasma etching with ammonia gas and (2) plasma polymerization with ammonia gas.

In one currently preferred embodiment of the present invention, the amine groups on the siloxane surface are reacted with epoxide-, or isocyanate-terminated poly-(ethylene oxide) (hereinafter referred to as "PEO"). After such reaction occurs, the siloxane surface contains PEO chains coupled to the amine groups. The PEO spacer chains are presently preferred because the PEO tends to minimize protein adsorption.

The unbound terminal end groups on the PEO chains readily react with the amine groups found in many bioactive molecules. Thus, various bioactive molecules may be covalently bonded to one end of the PEO chains in the same way that the other end of the PEO chain is covalently bonded to the siloxane blood-contacting surface.

Since the bioactive molecules are spaced away from the siloxane surface at one end of a long PEO chain, the bioactive molecules possess an activity approaching the activity of the bioactive molecules in solution. Because of this mobility of the bioactive molecules near the blood-contacting surface of the polymer, the effectiveness of the bioactive molecules is substantially greater than the same bioactive molecules bound directly to the blood-contacting surface. At the same time, the serious risks associated with systemic anticoagulation therapy are avoided.

Some typical bioactive molecules which may be immobilized on a blood-contacting surface within the scope of the present invention include: heparin, ticiopidine, prostaglandin $E_1$ ($PGE_1$), urokinase, plasmin, and tissue plasminogen activator (TPA).

Heparin inhibits the blood incompatibility reaction resulting in clotting and thromboemboli formation by interacting with antithrombin III and thrombin to inhibit the conversion of fibrinogen to fibrin.

Ticlopidine and prostaglandin $E_1$ inhibit the activation of platelets either by minimizing aggregation or inhibiting activation and the release of the intracellular platelet activators. Each drug has a slightly different mode of action. Urokinase, piasmin, and TPA are all serine proteases which lyse formed protein deposits and networks.

All of the above blood incompatibility reactions are activated by the introduction of a foreign material into blood. Nonetheless, the present invention is unique, because it applies a multi-dimensional approach to combatting the problem of thrombus formation.

Systems which have only heparin counteract just the clotting mechanism involving the formation of fibrin. Other systems attempt to inhibit platelet activation or aggregation. In classical anticoagulant therapy, only one of the many blood-material incompatibility reactions is inhibited. The present invention is multifunctional because it is capable of inhibiting a wide range of the blood-material incompatibility reactions.

It is, therefore, an object of the present invention to provide multifunctional thrombo-resistant compositions and methods of manufacture which counteract a wide range of blood material incompatibility reactions.

Another important object of the present invention is to provide multifunctional thrombo-resistant compositions and methods which do not inhibit the gas permeability of the blood-contacting surface.

An additional important object of the present invention is to provide multifunctional thrombo-resistant compositions and methods in which the bioactive molecules are covalently bound to the blood-contacting surface, thereby eliminating elution of the bioactive molecules into the blood plasma.

Still another object of the present invention is to provide multifunctional thrombo-resistant compositions and methods in which the bioactive molecules retain their activity after immobilization onto the blood-contacting surface.

These and other objects and features of the present invention will become more fully apparent from the following description and appended claims, or may be learned by the practice of the invention.

DETAILED DESCRIPTION OF THE PREFERRED EMBODIMENTS

The present invention provides a multifunctional thrombo-resistant coating for use with a blood-contacting surface of a medical device or implant. While it will immediately be appreciated that the present invention is applicable to a wide variety of medical device and implants, the coatings of the present invention are particularly suited for use with blood gas exchange devices. In any blood gas exchange device it is critical to both minimize thrombus and emboli formation, while at the same time preserving the gas exchange capabilities of the device.

Accordingly, for purposes of illustration, the coatings of the present invention are discussed with respect to one such blood gas exchange device (as described in the above-identified copending patent application entitled "Apparatus and Method for In Vivo Extrapulmonary Blood Gas Exchange"); however, it is not intended that the invention is to be construed as limited for use on only such devices.

A. Multifunctional Bioactive Molecules

To minimize the thrombo-resistant properties of any blood-contacting surface within the scope of the present invention, a wide variety of bioactive molecules which counteract specific blood-material incompatibility reactions are immobilized or linked to the blood-containing surface. It is an important feature of the present invention that a plurality of different bioactive molecules can be immobilized on the surface in order to inhibit a plurality of blood-material incompatibility reactions.

These bioactive molecules inhibit blood material incompatibility reactions such as: coagulation and thrombis formation; platelet destruction, injury, entrapment, and aggregation; complement activation; and protein adsorption. Table I provides a summary of the various bioactive molecules which may be used within the scope of the present invention to combat blood-material incompatibility reactions.

TABLE I

| BLOOD INCOMPATIBILITY REACTION | BIOACTIVE SUBSTANCE | TYPE OF BIOACTIVITY |
| --- | --- | --- |
| Extrinsic coagulation pathway activation | Heparin | Interruption of the conversion of fibrinogen to fibrin |
| Platelet destruction and injury, adhesion, and aggregation | Prostaglandin $E_1$ ($PGE_1$) | Inhibits platelet shape change, platelet factor release, secretion and aggregation |
|  | Ticlopidine | Protects platelets and inhibits platelet aggregation |
| Fibrin Formation | Plasmin | Lyses fibrin |
|  | Urokinase | Converts plasminogen to plasmin, general proteolytic enzyme. |
|  | TPA | Activates plasminogen |
| Protein adsorption | Poly(ethylene oxide) | Minimizes and prevents protein adsorption |
| Complement activation | FUT-175 | Inhibits $C1\bar{r}$, $C1\bar{s}$, thrombin, and kallikrein |

The various bioactive molecules immobilized onto the surface give the blood-contacting surface a multifunctional thrombo-resistant coating. The term "thrombo-resistant" is generally used herein to generically represent the action of inhibiting the variety of blood incompatibility reactions discussed above. The surface is multifunctional because a plurality of different bioactive molecules are linked to the surface in a sufficient concentration to counteract a wide range of blood-material incompatibility reactions.

As mentioned above, an important feature of the present invention is the multifunctional inhibition of a plurality of blood incompatibility reactions. Hence, the present invention is in contrast to traditional techniques which deal with a single bioactive molecule and a single aspect of the blood-material incompatibility reactions. Thus, despite substantial surface contact with blood, thrombus formation on the surface of the medical device or implant (e.g., a blood gas exchange device) is inhibited/counteracted according to the compositions and methods within the scope of the present invention.

It will be appreciated that Table I lists only a few of the bioactive substances which inhibit the identified blood-material incompatibility reactions and that other bioactive substances may be used in accordance with the present invention to make a surface thrombo-resistant. As is discussed hereinafter, another important feature of the bioactive molecules used in the present invention is the availability of a primary amine (or other suitable functional groups) to react with the unbound functional end group on a molecule attached to the substrate surface.

B. Blood Gas Exchange Device

The blood gas exchange devices to which the present invention is particularly applicable include both "sheet" membrane and tubular "membrane" oxygenators. Numerous oxygenators of these types are well known in the prior art.

For purposes of illustration, one blood gas exchange device to which the present invention is applicable includes a dual lumen tube containing two coaxial lumens. The outer lumen opens into a proximal chamber to which the proximal ends of a plurality of elongated gas permeable tubes are attached. The inner lumen extends past the outer lumen and passes among the gas permeable tubes. Both the inner lumen and the distal ends of gas permeable tubes open into a distal chamber.

The device is inserted into the patient's venae cavae through an incision made in either the common femoral vein or the external iliac vein. The gas permeable tubes are crimped in order to maintain the tubes in a spaced relation one from another so that the blood may flow freely between and around the tubes, thereby enhancing the blood surface contact with the gas permeable tubes.

One of either the inner or outer lumens is connected a source of oxygen-rich gas. The other lumen is connected to an exhaust tube or other means for allowing the gas flow out of the device. The oxygen-rich gas flows through the gas permeable tubes. As venous blood flows around the gas permeable tubes, oxygen passes from the tubes into the blood, thereby causing blood oxygenation, and carbon dioxide passes from the blood into the tubes and out of the body.

One of the primary goals of a blood gas exchange device (whether or not it has the specific configuration discussed above) is to maximize the gas transfer surface area in contact with the blood. Unfortunately, as the surface area of a foreign device in contact with blood increases, the risk of triggering a host of blood-material incompatibility reactions also increases.

Traditionally, as mentioned above, when a large quantity of blood contacts a foreign surface, systemic anticoagulants or thrombolytic agents are administered. Extreme care must be taken when administering any anticoagulants or thrombolytic agents to avoid the potential risk of serious hemorrhage both internally and externally. Thus, it is important that the blood-contacting surface of a blood gas exchange device is both gas permeable and thrombo-resistant. For these reasons, when the present invention is used with a blood gas exchange device, the blood-contacting surface is preferably constructed of a thin siloxane polymer.

C. Linking the Bioactive Molecules onto the Blood-Contacting Surface

For purposes of illustration, reference will be made to "linking" or "immobilizing" bioactive molecules on the blood-contacting substrate surface of a blood gas exchange device. It will be readily appreciated that the principles and teachings of the present invention are generally applicable to most other medical devices and implants which contact blood and have a problem with thrombus and emboli formation.

Moreover, it will be appreciated that the term "immobilized" is being used in the sense that the bioactive molecules are covalently linked or "tethered" to a specific portion of the polymer substrate vis-a-vis free floating in the blood. Therefore, even though the bioactive molecules may not be directly attached to the blood-contacting surface (as discussed in greater detail below), the bioactive molecules are closely associated to the surface through a linkage such that the blood cells contact the bioactive molecules as they come proximate to the blood-contacting surface.

Most of the bioactive molecules described above are capable of being immobilized to the blood-contacting surface of the blood gas exchange device through PEO coupling molecules. PEO is the preferred coupling molecule, because PEO itself functions to minimize protein adsorption. This property of PEO is believed to be due in part to PEO's unique hydrophobic and hydrophylic characteristics.

Because the blood-contacting surface of the blood-gas exchange device is preferably constructed of siloxane, the inherent inertness of the siloxane polymer minimizes thrombus formation. However, this same inherent inertness of the siloxane significantly complicates the method of immobilizing the bioactive molecules to the surface.

To overcome the inertness of the siloxane, functional groups are introduced on the siloxane surface. These functional groups provide distinct and predictable sites for reaction with PEO. The PEO chains are then coupled to the blood-contacting surface through the functional groups. In the currently preferred embodiment of the present invention, amine groups are introduced onto the siloxane surface.

1. Introduction of Amine Groups by Plasma Etching

One proposed method for introducing amine groups on the siloxane surface within the scope of the present invention involves plasma etching with ammonia gas. In the blood-gas exchange device of the present invention, microporous hollow fibers coated with a plasma-polymerized siloxane are used as the substrate. These fibers are subjected to additional plasma exposure in the presence of ammonia gas.

The term "plasma" refers to a partially ionized gas which is in a non-equilibrium state. The electrons can react with gases or other materials present in the system producing a number of reactive particles and radiation such as cations, anions, free radicals, excited molecules, ultraviolet radiation, etc. By nature, plasma reactions are somewhat uncertain and unpredictable.

The pressure, temperature, gas low rates, exposure time, power, and other parameters in a plasma process are highly interdependent and highly dependent upon the size and geometry of the plasma chamber. The power per unit area is an important parameter in reproducibly controlling the chemical structure of the resulting polymer. However, since plasma etching procedures and techniques are well known, a detailed discussion of each of the process parameters is not provided.

One plasma chamber used for plasma etching within the scope of the present invention has a volume of about 20,000 $cm^3$ and capacitively coupled plate electrodes. The plasma chamber was obtained commercially from Plasma Science (Belmont, Calif.), and modified by the inventors by removing the two lower electrode plates so that the chamber would accommodate a smaller cylindrical plasma chamber. The siloxane miasma-coated fibers, having a surface area of about 2,100 $cm^2$, are exposed to ammonia having a flow rate in the range of from about 100 micromoles per second no about 300 micromoles per second, at an absolute pressure in the range from about 100 millitorr to about 200 mtorr. The exposure time ranges from about thirty (30) seconds to about three (3) minutes. The currently preferred exposure time is in the range from about 60 seconds to about 120 seconds. A radio frequency of 13.56 MHz in the range from about 20 watts to about 250 watts generates sufficient energy to break the molecular bonds of both the ammonia gas and the siloxane surface.

Another plasma chamber used for plasma etching has a volume of about 28.7 $cm^3$ and capacitively coupled copper collar electrodes located outside the tube. The chamber is cylindrical, having a diameter of about one centimeter and a length of about 25 centimeters. The siloxane plasma-coated fibers, having a surface area of about 3.03 $cm^2$ are exposed to ammonia having a flow rate in the range from about 10 micromoles per second to about 120 micromoles per second, at an absolute pressure in the range from about 100 mtorr to about 200 mtorr. The exposure time ranges from about 30 seconds to about 120 seconds. A radio frequency of 13.56 MHz in the range from about 20 watts to about 150 watts generates sufficient energy to break the molecular bonds of both the ammonia gas and the siloxane surface.

It will be appreciated by those skilled in the art than in a differently configured plasma chamber, the ammonia flow rate, power, chamber pressure, and exposure time may be outside the ranges of that set forth for the embodiment discussed above. Nevertheless, current experimental testing suggests that the power should relate to the monomer or gas flow rate such that W/FM is in the range from 30–50 megajoules/Kg, where W is the discharge power in joules per second, F is the mass flow rate in moles per second, and M is the molecular weight of a gas (g/mole). However, this value (W/FM) does not take into consideration the power density which is determined by the volume of the plasma. Because the minimum wattage necessary for the plasma polymer of a given monomer differs significantly from than of another monomer at a given pressure, it becomes immediately obvious that W, wattage per square centimeter, or current density alone is not sufficient to describe the conditions of plasma polymerization.

Hence, the flow rate, power, and pressure may well be outside of the ranges given.

In light of these stoichiometric relationships, those skilled in the art can readily determine relationships between the flow rate, the pressure, and the exposure times of the siloxane surface to the ammonia.

Plasma may be generated by a number of methods including combustion, flames, electric discharge, controlled nuclear reactions and shocks. The most obvious and commonly used is the electric discharge. Radio frequency (RF) or microwave discharge are mainly used for polymerization reactions. For the commercial RF generators, the frequency is dictated by the Federal Communications Commission and is set at 13.56 MHz.

Ammonia derivatives, existing as free radicals and ions react with each other and with the siloxane surface, thereby introducing amine functionalities onto the siloxane surface. Analysis by electron spectroscopy for chemical analysis ("ESCA") establishes that nitrogen in the form of amine functionalities can be introduced onto the surface on the order of from about two (2) to about eight (8) total atomic percent. ESCA measurements of about three total atomic percent have been found to result in a satisfactory end product. Other polymers not as inert as siloxanes are capable of incorporating much higher amounts of nitrogen.

It should be noted that ESCA analyzes only the top 50–100 angstroms of a surface. Analysis of bulk structure below the sampling depth is not possible with ESCA. In addition, the atomic percent reported by ESCA is for the entire volume analyzed (i.e., the top 50–100 angstroms). Thus, 3% nitrogen does not correspond with 3% of the surface atoms being nitrogen. This is because the nitrogen atoms would be found only on the surface and atoms (i.e. carbon/silicone) from below the surface are also detected.

Nevertheless, ESCA does establish the existence significant amounts of nitrogen at or near the surface. Moreover, analysis of percent nitrogen provides a valuable approximation for the number of free amines on the surface. The quantity of amines bound to the surface directly affects the coupling efficiency of the PEO or bioactive molecules. Thus, the more amine groups, the more PEO coupling sites.

From the foregoing, it will be appreciated than the parameters associated with ammonia etching are highly interdependent and dependent upon the specific plasma chamber. The following examples illustrate this interdependence. One skilled in the art would appreciate that the parameters described in the following examples can be modified when using a different sized plasma chamber.

EXAMPLE 1

Amine groups were introduced onto the surface of a siloxane-coated hollow fiber within the scope of the present invention by plasma etching in the presence of ammonia, Celanese X20-240 microporous hollow gibers were used as the substrate, The fibers were coated with plasma-polymerized siloxane, The fibers were subjected to additional plasma exposure in the presence of ammonia gas by passing the fibers through a cylindrical plasma chamber one centimeter in diameter and approximately 25 centimeters long with two copper collar electrodes capacitively coupled to the chamber. The surface area of the fibers was about 3.0 $cm^2$. Ammonia gas was introduced into the plasma chamber at a flow rate of 30 micromoles per second at 110 mtorr absolute pressure. The fibers were exposed to 45 watts at a radio frequency of 13.56 MHz for 60 seconds.

According to ESCA analysis, nitrogen in the form of amine functionalities was introduced onto the surface on the order of three total atomic percent. As discussed hereinafter, this amount of nitrogen provides sufficient amine reaction sites for attachment of the PEO and the multifunctional bioactive molecules.

EXAMPLE 2

Amine groups were introduced onto the surface of a siloxane-coated hollow fibers according to the procedure of Example 1, except that the ammonia gas was introduced into the plasma chamber at a flow rate of 120 micromoles per second at 110 mtorr absolute pressure. The fibers, having a surface area of about 3.0 $cm^2$, were exposed to 60 watts at a radio frequency of 13.56 MHz for 30 seconds.

Utilizing the procedures of Example 2, nitrogen in the form of amine functionalities as introduced into the surface as analyzed by ESCA on the order of three total atomic percent. While the flow rate of the ammonia gas in the plasma chamber was four times greater than that of Example 1, no significant increase in the amount of amine functionalities on the siloxane surface were observed.

EXAMPLE 3

Amine groups were introduced onto the surface of siloxane-coated hollow fibers according to the procedure of Example 1, except that the fibers were exposed to 20 wants at a radio frequency of 13.56 MHz for two minutes.

Utilizing the procedures of Example 3, nitrogen in the form of amine functionalities were introduced onto the surface as analyzed by ESCA on the order of two total atomic percent. While the fibers of Example 3 were exposed to only 40% of the power used on the fibers of Example 1, there was only a slight decrease in the amount of amine functionalities on the siloxane surface.

EXAMPLE 4

Amine groups were introduced onto she surface of siloxane-coated hollow fibers according to the procedure of Example 1, except that the ammonia gas was introduced into the plasma chamber at a flow rate of 120 micromoles per second at 110 mtorr absolute pressure. The fibers were exposed to 20 watts at a radio frequency of 13.56 MHz for 30 seconds.

Utilizing the procedures of Example 4, nitrogen in the form of amine functionalities was introduced onto surface as analyzed by ESCA in less than two total atomic percent. Fiber exposure to 20 watts for 30 seconds was insufficient for adequate nitrogen incorporation.

EXAMPLE 5

Amine groups were introduced onto the surface of a siloxane substrate within the scope of the present invention by plasma etching in the presence of ammonia. The dimensions of the plasma chamber were fifteen inches long, twelve inches wide and five inches high. The electrodes were in the form of two parallel plates capacitively coupled in the chamber. The siloxane-coated substrate is comprised of a siloxane coating on a polymeric surface. The siloxane surface, with a surface area of 2,100 cm² is subjected to additional plasma exposure by introducing ammonia gas into the plasma chamber at the flow rate of 288 micromoles per second at 180 mtorr absolute pressure. The siloxane surface is exposed to 186 watts at a radio frequency of 13.56 MHz for two minutes.

According to ESCA analysis, nitrogen species are introduced onto the surface on the order of 3.5 total atomic percent.

EXAMPLE 6

Amine groups were introduced on the surface of a siloxane-coated polyethylene substrate according to the procedure of Example 5, except that the siloxane-coated substrate is exposed to 150 watts at a radio frequency of 3.56 MHz for a period of 90 seconds.

Utilizing the procedures of Example 6, nitrogen containing functionalities are introduced onto the siloxane-coated surface as analyzed by ESCA on the order of four total atomic percent.

EXAMPLE 7

Amine groups were introduced onto the surface of a siloxane substrate within the scope of the present invention by plasma etching in the presence of ammonia. The siloxane substrate, comprised of a siloxane coated glass slide, was subjected to additional plasma exposure by placing the substrate into the cylindrical plasma chamber one centimeter in diameter and approximately 25 centimeters long. Ammonia gas was introduced into the plasma chamber at a flow rate of 12 micromoles per second. The pressure within the chamber was maintained at 180 mtorr absolute pressure. The siloxane substrate was exposed to 100 watts at a radio frequency of 13.56 MHz for ten minutes.

According to ESCA analysis, nitrogen in the form of amine functionalities was introduced onto the surface on the order of eight total atomic percent. The higher incorporation of nitrogen was attributed to a different type siloxane substrate and an increase in power and exposure time made possible because the glass substrate is nonfragile and can withstand prolonged plasma exposure.

EXAMPLE 8

Amine groups were introduced onto the surface of a siloxane substrate within the scope of the present invention by plasma etching in the presence of ammonia. The siloxane substrate, comprised of a methyl vinyl siloxane coated onto a glass slide, was subjected to plasma exposure by placing the substrate into the cylindrical plasma chamber one centimeter in diameter and approximately 25 centimeters inches long. Ammonia gas was introduced into the plasma chamber at a flow rate of 12 micromoles per second. The pressure within the chamber was maintained at 180 mtorr absolute pressure. The siloxane substrate was exposed to 50 watts at a radio frequency of 13.56 MHz for 15 minutes.

According to ESCA analysis, nitrogen in the form of amine functionalities was introduced onto the surface on the order of 22 total atomic percent. The higher incorporation of nitrogen was attributed to a different type of siloxane substrate and an increase in power and exposure time made possible because the silicone-coated glass substrate was nonfragile and can withstand prolonged plasma exposure.

2. introduction of Amine Groups by Plasma Polymerization

Another method for introducing the amine functionalities onto the blood-contacting surface of the siloxane polymer is to introduce the amine groups during the siloxane polymerization itself. This process, known as plasma polymerization or glow discharge polymerization, is achieved by introducing a siloxane monomer vapor and ammonia gas simultaneously in the presence of the plasma. The same type of tubular chamber used for plasma etching (Examples 1–4) may be used for plasma polymerization.

Two opposing processes occur simultaneously during plasma polymerization: (1) polymer formation which leads no deposition of a material and (2) ablation which leads to removal of material. Generally, at very low flow rates there is little polymer deposition and the deposition rate decreases with increasing discharge wattage. At higher flow rates, the deposition increases (linearly), but reaches a maximum with increasing discharge wattage and then ablation becomes more predominant.

The amount and relative position of polymer deposition is influenced by three geometric factors: (1) location of electric energy input; (2) monomer flow; and (3) substrate position within the reactor relative to the glow region. These factors are only important in batch polymerization processes. In the case of hollow fibers, which are pulled continuously through the plasma chamber, the influence off the substrate position is averaged over the length of the fibers.

The population of energetic species that contribute to the direct formation of plasma polymer is not directly or uniquely related to the power input into the system. The intensity of a non-polymer forming plasma (i.e., plasma etching) is dependent on the combined factors of pressure and discharge power as well as on other factors of the discharge system such as distance between electrodes, surface area of electrodes, and total volume of the reactor.

Various parameters have been used to describe the energy input of plasma polymerization such as current density, current and voltage, or wattage. These parameters may have varying degrees of applicability to an inductively coupled RF discharge system. However, such parameters are insufficient to describe the change in total volume of plasma and the plasma polymerization that takes place in the volume, although certain correlations can be found between the deposition rates and these parameters, but only for a given set of experimental conditions.

An important feature of the present invention, particularly for use with a blood oxygenator, is the creation of a smooth, continuous (pin-hole free) thin coating over the pores of the hollow fiber. The thickness of this coating can be determined gravimetrically, and the continuity of the coating can be determined by the permeability. These factors, along with the chemical composition (i.e., carbon, silicone, oxygen, nitrogen percentages, determined by ESCA) are some of the values which change as plasma parameters are modified.

The chemical composition of the plasma coating affects the gas permeability. For example, as the cross-link density increases, the permeability decreases. Factors which affect the cross-link density include: pressure, power, flow rate, and position within the reactor. Gas permeability is also influenced by the plasma deposition thickness and the completeness of coverage of the pores.

In order to achieve plasma polymerization, the siloxane monomer and ammonia gas in a concentration ratio in the range from about 1:10 to about 10:1 (and preferably about 3:1, siloxane monomer to ammonia) and at an absolute pressure in the range from about 100 to about 200 mtorr, are introduced into the plasma chamber. One presently preferred siloxane monomer is tetramethyldisiloxane, commonly known as "TMDS." Other suitable siloxane monomers include hexamethyldisiloxane, octamethyltrisiloxane, hexamethyicyclotrisiloxane and octamethylcyclotetrasiloxane.

In one embodiment within the scope of the present invention, siloxane monomer with a flow rate in the range from about ten micromoles per second to about 30 micromoles per second and ammonia gas with a flow rate in the range from about ten micromoles per second to about 30 micromoles per second are introduced into the plasma chamber. Capacitively coupled power in the range from about 45 to about 60 watts at a frequency of 13.56 MHz of a radio frequency generator is applied to create the plasma.

The hollow fibers are pulled through the plasma zone such that the total residence time in the plasma is in the range from about 30 seconds to about 70 seconds. Nitrogen in the form of amine functionalities is introduced onto The siloxane surface as analyzed by ESCA on the order of about six (6) to eight (8) total atomic percent.

Care should be taken when polymerizing siloxane in the presence of ammonia that too much ammonia is not incorporated into the resulting polymer coating. It would be expected that as the concentration of nitrogen increases, the gas permeability of the polymer decreases. Accordingly, the percentage of the nitrogen functionalities in the siloxane coating should toe exceed about eight (8) total atomic percent; otherwise, the gas permeability may be significantly decreased.

As with plasma etching, power distribution in the plasma chamber used in this plasma polymerization process can be determinative of the process parameters used. The following examples illustrate this interdependence.

EXAMPLE 9

The surface of polypropylene hollow fibers was coated with a nitrogen-containing siloxane plasma polymer within the scope of the present invention by plasma polymerization in the presence of ammonia. Polypropylene microporous hollow fibers were used as the substrate.

The fibers were subjected to plasma polymerization by passing the fibers through a cylindrical plasma chamber one centimeter in diameter and approximately 25 centimeters long. Nine micromoles per second tetramethyldisiloxane along with three micromoles per second ammonia gas were introduced into the plasma chamber.

The plasma was struck at 150 watts using a radio frequency generator at a frequency of 13.56 MHz and then reduced to 45 watts following striking. A higher power is necessary to "strike" the plasma in order to initiate bond cleavage. Thereafter, the power is reduced before introducing the fibers into the plasma chamber, otherwise the high power could destroy the fragile fibers.

The pressure in the plasma chamber was maintained at 110 mtorr absolute pressure by use of a vacuum throttling valve. The fibers were pulled through the plasma zone such that the total residence time in the plasma was 60 seconds.

According to ESCA analysis, nitrogen containing functionalities were introduced and detected on the surface of the fiber on the order of six total atomic percent. presumably amine functionalities were incorporated into the bulk of the fiber as well. Scanning Electron Microscope analysis (SEM) demonstrated the thickness of the coating to be less than 1 micron.

EXAMPLE 10

The surface of polypropylene hollow fibers was coated with a nitrogen-containing siloxane plasma polymer according to the procedure of Example 9, except that the residence time of the fibers in the plasma was 70 seconds.

Utilizing the procedures of Example ! 0, nitrogen-containing functionalities were introduced throughout the bulk of the polymer with a surface concentration on the order of six total atomic percent as analyzed by ESCA. Gravimetric analysis of one meter of the fiber showed a gain of 0.7 milligrams. This indicated a coating of less than 1 micron.

EXAMPLE 11

The surface of polypropylene hollow fibers was coated with a nitrogen-containing siloxane plasma polymer according to the procedure of Example 9, except that the power was reduced to sixty (60) watts following striking.

Utilizing the procedures of Example 11 amine functionalities were introduced throughout the bulk of the polymer as analyzed by ESCA on the order of six total atomic percent. Gravimetric analysis of one meter of fiber indicated the thickness of the coating was 1.0 micron.

EXAMPLE 12

The surface of polypropylene hollow fibers was coated with a nitrogen-containing siloxane plasma polymer the scope of the present invention by plasma polymerization in the presence of ammonia. Celanese X20-240 microporous hollow fibers were used as the substrate.

The substrate is subjected to plasma polymerization by passing the substrate through a cylindrical plasma chamber 1 centimeter in diameter and 25 centimeters long with two sets of capacitively coupled electrodes (i.e., two hot and two ground). Nine micromoles per second of TMDS along with three micromoles per second of ammonia gas are introduced into the plasma chamber. The plasma is struck at 150 at a radio frequency of 13.56 MHz and then reduced to 60 watts after striking.

The pressure in the plasma chamber was maintained at 110 mtorr absolute pressure by use of a vacuum throttling valve. The total residence time of the siloxane-coated substrate in the plasma was 60 seconds.

ESCA analysis indicated approximately 6% nitrogen on the surface. Gravimetric analysis determined the coating be approximately 1.5 microns thick.

EXAMPLE 13

The surface of polypropylene hollow fibers was coated with a nitrogen-containing siloxane plasma polymer according to the procedure of Example 12, except that the pressure of the chamber was maintained at 180 mtorr.

Utilizing the procedures of Example 13, it was determined that melting of the fiber had occurred.

EXAMPLE 14

A siloxane coating containing nitrogen, hydroxyl and carbonyl functionalities was coated onto a glass substrate within the scope of the present invention by plasma polymerization in the presence of ammonia and water vapor. The glass substrate was subjected to plasma polymerization in the cylindrical plasma chamber described in Example 12 except that water vapor was introduced along with the ammonia and monomer. The water vapor flow tame was approximately three micromoles per second. The substrate was exposed to 60 watts for a period of four minutes. Analysis of the coating by ESCA determined that 7.5% carbonyl, 15% hydroxyl and 4% amine functionalities were present.

EXAMPLES 15-18

In Examples 15-18, the surface of polypropylene hollow fibers was coated with a siloxane plasma polymer according to the procedure of Example 11, except that the ratio of TMDS to ammonia was varied from 10:1 to 1:10 in a constant molar gas flow rate of 12 micromoles per second. The chemical composition of the resulting siloxane plasma polymers, as analyzed by ESCA, are see forth below:

TABLE II

| Example | TMDS:Ammonia | C % | O % | Si % | N % |
|---|---|---|---|---|---|
| 15 | 10:1 | 47 | 16 | 37 | 0 |
| 16 | 3:1 | 45 | 21 | 38 | 6 |
| 17 | 1:1 | 48 | 24 | 30 | 4 |
| 18 | 1:10 | 43 | 24 | 32 | <1 |

These results indicate that a ratio of TMDS to ammonia of about 3:1 produces a siloxane plasma polymer with a high percent nitrogen incorporation.

3. Amine Functionalities on the Siloxane Surface

Both ammonia etching and plasma polymerization with ammonia result in amine incorporation into or onto the siloxane polymer. ESCA analysis of the resulting surface demonstrates the existence of Si—H bonds, C—N bonds, amine (NH$_2$) groups, and carbonyl (C=O) groups. In addition, the surface likely includes reactive radicals (e.g., •CH$_2$ and •NH). While the exact surface structure resulting from 25 these reaction processes is not known, the resulting surface structure is believed to be a combination of a number of possible bond and group configurations including:

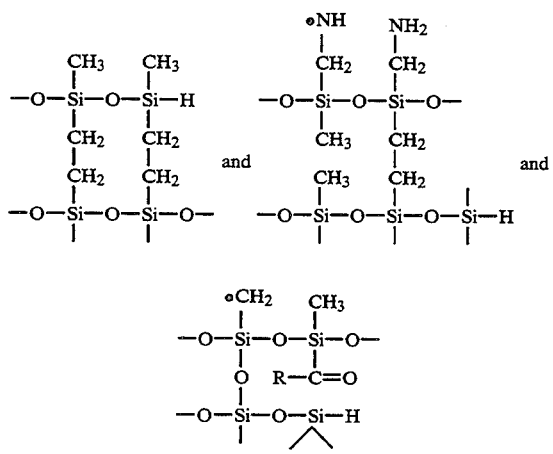

R may be H or OH.

The degree of cross-linking (i.e., the number of bonds formed from methyl radicals on adjacent polymer chains reacting together to form an ethylene unit between chains) is totally dependent upon the reaction parameters. Any polymerization performed using plasma results in a "plasma polymer." The structure of a plasma polymer is significantly different from those resulting from other known polymerization mechanisms; these plasma polymers are by nature "ill-defined."

It will be appreciated that an important aspect of the present invention is the incorporation of amine functionalities (which are available for reaction with PEO) on the blood-contacting surface. Hence, other plasma reaction processes which introduce amine onto the surface are useful as a part of the present invention.

For example, another possible process for introducing amine functionalities on the blood-contacting surface would be to coat the surface with siloxane monomer in the plasma, and then introduce another polymerizable gas which contains amine groups. One potentially suitable amine-containing polymerizable gas is allylamine.

The allylamine may be introduced while the surface is in the plasma or shortly after the plasma has been turned off. Such polymerization processes could result in an extremely thin polymer layer, probably only a few atomic layers thick on top of the siloxane, with a high percentage of primary amine groups. Theoretical calculations suggest that nitrogen containing functional groups could be incorporated onto the siloxane on the order of about twenty atomic percent.

Such a thin polymer layer should not adversely affect the overall gas permeability of the siloxane or its other mechanical properties. However, if the allylamine were polymerized to form more than just a few atomic layers, the gas permeability of the siloxane substrate might be significantly reduced. Since allylamine polymerization mends to preserve the amine groups rather than forming ammonia byproducts, an allylamine plasma polymerization has the potential of introducing a significantly higher percentage of potentially reactive amine groups on the siloxane surface.

In addition, depending on the type of siloxane monomer used to form the siloxane surface, nitrogen gas is a suitable alternative to ammonia gas in both the plasma etching and plasma polymerization processes described above. Nitrogen gas initially introduces both amine groups and nitrogen radicals onto the siloxane surface, but upon exposure to water vapor, the nitrogen radicals quickly quench to form amine groups. Because nitrogen is less expensive than ammonia, the use of nitrogen gas can significantly reduce the costs associated with the plasma process described above.

Although the foregoing discussion has focused on the incorporation of amine groups onto the siloxane surface, it will be appreciated that the principles within the scope of the present invention may be readily adapted to incorporate other reactive functional groups onto the siloxane surface.

Thus, an important aspect of the invention is the incorporation of any reactive functional group such as hydroxyl, carbonyl, or carboxylic groups onto the siloxane surface. These functional groups would provide a chemical "handle" on the otherwise inert siloxane surface to which PEO and bioactive molecules may be bound.

In this regard, other gases and monomers may be used during the plasma etching or plasma polymerization processes to introduce reactive functional groups. As illustrated in Example 14, above, the introduction of water vapor during the plasma polymerization process has been found to introduce carbonyl and hydroxyl functionalities onto the siloxane surface, as well as amine groups.

It has been found that plasma etching with argon gas or oxygen gas causes destruction of the hollow fibers (as measured by decrease in tensile strength) in less than one minute of exposure. On the other hand, similar exposure to ammonia gas did not destroy the hollow fibers. This is one reason why ammonia is currently preferred for plasma etching. Nevertheless, if the substrate is not fragile like the hollow fibers, then argon and oxygen plasmas may be used to introduce reactive functional groups onto the siloxane surface.

The surfaces which emerge from the plasma in any of the processes discussed above are highly reactive. While exact molecular analysis is difficult, the surfaces likely contain some radicals which are available for reacting with almost any species containing double bonds which come into contact with the siloxane surface.

4. Reaction of Amine Functionalities with PEO

Immediately upon removal from the plasma, the surfaces of the hollow fibers may be reacted with the terminal end groups of unbranched PEO. The PEO functions as an extended flexible spacer to tether bioactive molecules away from, but in close proximity to, the siloxane surface, thereby avoiding problems of steric hindrance of adjacent bioactive molecules which may then be coupled to the siloxane surface. Moreover, as discussed above, the PEO itself also assists in minimizing protein adsorption on the siloxane surface.

A PEO solution is prepared by dissolving poly(ethylene oxide) bis(glycidyl ether) (commonly known as "PEO diglycidyl ether," or "polyoxyethylene diglycidyl ether") into a solution containing formamide and water. The concentration of formamide in water is in the range from about 25% to about 35% (preferably about 30%). The PEO must be in excess to minimize "looping" of the PEO by both reactive ends coupling to the amine groups on the surface. Typical PEO concentrations are in the range from about 5% to about 36%, and preferably about 9% to about 18%.

Poly(ethylene oxide) bis(glycidyl ether) of any molecular weight may be used. However, for maximum protein resistance, the range should be from about 1500 to about 6000 and preferably in the range from about 3000 to about 4000. It has been found that PEO within this molecular weight range minimizes the protein adsorption and maximizes repulsion of platelets from the surface. There is a balance between chain length and stability as well. Longer chains are more susceptible to chain scission. Shorter PEO chains are less flexible which reduces their protein-resistant properties.

Many terminal reactive groups on PEO may be used depending upon the functionality on the siloxane to which coupling is desired. In the case of amine groups on the siloxane surface, suitable terminal groups include epoxides or isocyantes. In the case of carbonyl groups on the siloxane surface, amine terminated PEO would be appropriate. In any event, only those PEO chains with two reactive functional groups would be available for coupling to a surface and to a bioactive molecule.

In the case of epoxide-terminated PEO, the percent epoxide within the PEO varies depending upon the manufacturer and can vary from about 10% to greater than 75% 1.5 epoxide. The percentage epoxide directly affects the coupling efficiency. Therefore, if 100% of all PEO chains contain terminal epoxide groups, theoretically all could bind not only to the surface but also be available for binding bioactive molecules.

The plasma-coated fibers of the blood gas exchange device are allowed to sit in the PEO solution, without agitation, for about ten hours. It has been found that the amount of PEO coupling (as determined by ESCA) does not significantly increase after twelve (12) hours. In addition, increasing the concentration of PEO (to about 36 weight percent in the solvent) does not significantly increase the amount of coupling over the same time interval. The temperature of the PEO solution is preferably maintained at ambient temperature, in the range from about 20° C. to about 30° C.

After removal from the PEO solution, the coated hollow fibers are rinsed with purified water to remove any unbound PEO. The epoxide groups located at the terminal ends of the PEO chains have reacted with the amine groups located on the siloxane surface as shown below:

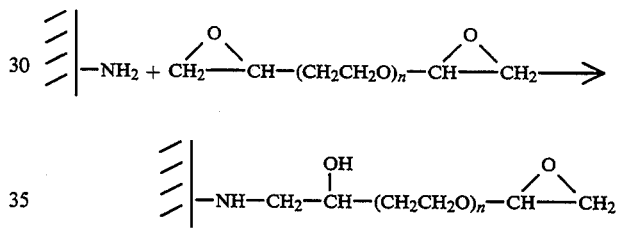

Due to the large excess of PEO used and reaction conditions, only one end of the PEO chain is bound to an amine group on the siloxane surface. As a result, each PEO chain contains an unreacted epoxide group at its unbound end. In addition, any carbon radicals (•CH₂) remaining on the surface following plasma polymerization would not be expected to react with the epoxide groups and would continue to be reactive.

Alternatively, it has been found than the PEO chains may also be suitably terminated with isocyanate functionalities. The amine groups located on the siloxane surface react with the isocyanate in much the same way as the amine nitrogen reacts with the epoxide terminated PEO as shown below.

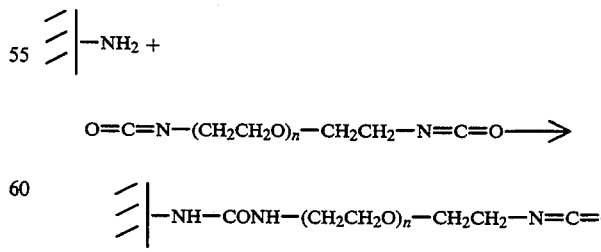

The epoxide effectively reacts with the electron-rich amine nitrogen because epoxide is a highly strained three-member ring. It also contains an electron depleted carbon atom. The epoxide efficiency is due mainly to the strained ring. The isocyanate reacts well with the amine nitrogen because the isocyanate carbon is accessible and electron depleted.

It will be appreciated that the PEO chains may be suitably terminated with other functional groups such as imidazole carbonyl. The important considerations in selecting a suitable functional group are its attachability to PEO and its activity with amines. Nevertheless, the epoxide and isocyanate terminated PEO have been found to produce a satisfactory product without elaborate and complex reaction conditions.

Despite the process used to incorporate the amine functionalities onto the surface of the polymeric substrate, the PEO can readily react with the amine groups to attach the PEO to the siloxane (or other suitable polymer) substrate, as shown in the following examples.

EXAMPLE 19

Siloxane-coated hollow fibers on which amine functicnalities have been incorporated onto the siloxane surface according to the procedures of Example 1 were reacted with a solution containing poly(ethylene oxide) bis(glycidyl ether). This PEO solution was prepared by dissolving eighteen grams of PEO bis(glycidyl ether) having average molecular weight of 3,500 in 100 ml of a solvent containing 35 parts formamide and 65 parts purified water.

The hollow fibers were reacted with the PEO solution for ten hours without agitation. The PEO solution temperature was maintained at ambient temperature within the range from about 20° C. to about 30° C. Upon removal from the PEO solution, the hollow fibers were rinsed with 100 ml of purified water to remove any unbound PEO bis(glycidyl ether).

ESCA analysis indicated that 17% of the carbon on the surface of the fiber was in the form of an ether functionality. It was assumed that all ether-type of carbon atoms were due to PEO coupling.

EXAMPLE 20

Siloxane-coated hollow fibers onto which amine functionalities had been introduced according to the procedures of Example 1 were reacted with the PEO solution in accordance with the procedures of Example 19 with the exception that the hollow fibers were reacted with the PEO solution for 72 hours.

Upon testing (as described in detail in Example 19), it was found that the PEO had reacted with the amine groups on the siloxane surface. The additional reaction time resulted in only slightly increased PEO concentration on the surface.

EXAMPLE 21

Siloxane-coated hollow fibers on which amine functionalities have been incorporated onto the siloxane surface according to the procedure of Example 9 were reacted with the PEO solution in accordance with the procedure of Example 19.

ESCA analysis indicated that 22% of the carbon on the surface of the fiber was in the form of an ether functionality. It was assumed that all ether-type carbon atoms were due to PEO coupling.

EXAMPLE 22

Siloxane-coated fibers onto which amine functionalities had been introduced according to the procedure of Example 9 were reacted with the PEO solution in accordance with the procedure of Example 20.

ESCA analysis Indicated that 22% of the carbon on the surface of the fiber was in the form of an ether functionality. It was assumed that all ether-type carbon atoms were due to PEO coupling. This demonstrates that the additional reaction time did not result in an increased PEO concentration on the surface.

EXAMPLE 23

Polyethylene microporous hollow fibers with a siloxane coating onto which amine functionalities had been introduced according to the procedure of Example 1 were reacted with the PEO solution in accordance with the procedure of Example 19 with the exception that the PEO had a molecular weight of 600 at a concentration of 5%.

ESCA analysis indicated that 50% of the carbon on the surface of the fiber was in the form of an ether functionality. This demonstrates that higher efficiency coupling can be obtained using lower molecular weight PEO.

EXAMPLES 24–29

In Examples 24–29, amine-containing siloxane-coated hollow fibers prepared in accordance with Examples 2–4 and 10–12, respectively, are reacted with the PEO solution according to the procedures set forth in Example 19.

Upon analysis, it is determined that 15–22% of the carbon on the surface is in the form of an ether functionality. It is assumed that all ether-type carbon atoms are due to PEO coupling. The higher the nitrogen lo incorporation, the higher the PEO coupling efficiency.

EXAMPLES 30–34

In Examples 30–34, the siloxane-coated polymeric substrate incorporating the amine functionalities prepared according to the procedures of Examples 5–8 and 14, respectively, are reacted with the PEO solution in accordance with the procedures of Example 19.

Upon analysis, it is determined that 15–25% of the carbon on the surface of the hollow fibers is in the form of an ether functionality. It is assumed that all ether-type carbon atoms are due to PEO coupling.

EXAMPLES 35–40

In Examples 35–40, amine-containing siloxane-coated hollow fibers are prepared according to the procedures of Examples 2–4 and 10–12, respectively, are reacted with a PEO solution in accordance with the procedures set forth Example 20.

Upon analysis, it is determined that 15–25% of the carbon on the surface of the hollow fibers is in the form of an ether functionality. It is assumed that all ether type carbon atoms are due to PEO coupling.

EXAMPLES 41–45 in Examples 41–45, siloxane-coated polymeric substrates onto which amine functionalities had been introduced according to the procedures of Examples 5–8 and 14, respectively, are reacted with the PEO solution described in, according to the procedures of Example 20.

Upon analysis, it is determined that 15–25% of the carbon on the surface is in the form of an ether functionality. It is assumed that all ether-type atoms are due to PEO coupling.

EXAMPLE 46

Amine-containing siloxane-coated hollow fibers, prepared in accordance with the procedures of Example 1, are reacted with a PEO solution prepared by dissolving five grams of PEO bis(isocyanate) having an average molecular weight of 3500 into 100 ml of dry methylene chloride. The reaction is performed under a nitrogen atmosphere.

The hollow fibers are reacted with the PEO solution for ten hours without agitation. The PEO solution temperature is maintained at ambient temperature within the range of from about 20° C. to about 30° C. Upon removal from the PEO solution, the hollow fibers are rinsed with 100 ml of methylene chloride to remove any unbound PEO bis(isocyanate).

Upon analysis, it is determined that 45% of the carbon atoms on the surface are attributed to PEO attached to the siloxane surface of the hollow fibers.

EXAMPLE 47

In Example 47, amine-containing siloxane-coated hollow fibers prepared in accordance with the procedures of Example 1, are treated with a solution containing poly(ethylene oxide) bis(isocyanate), which is prepared by dissolving three grams of PEO bis(isocyanate) having an average molecular weight of 3500 into 100 ml of dry methylene chloride. The reaction is performed under a nitrogen atmosphere.

The hollow fibers are reacted with the PEO solution for 72 hours without agitation. The PEO solution temperature is maintained at ambient temperature within the range of from about 20° C. to about 30° C. Upon removal from this PEO solution, the hollow fibers were rinsed with 100 ml of methylene chloride to remove any unbounded PEO bis(isocyanate).

Upon analysis, it is determined that 40% of the carbon atoms on the surface are attributed to PEO attached to the surface of the hollow fibers.

EXAMPLES 48–54

In Examples 48–54, siloxane-coated hollow fibers on which amine functionalities had been introduced, prepared in accordance with the procedures of Examples 2–4 and 9–12, are reacted with a PEO solution according to the procedures set forth in Example 46.

Upon analysis, it is determined that 55% of the carbon atoms on the surface are attributed to PEO attached to the siloxane surface of the siloxane-coated hollow fibers.

EXAMPLES 55–61

In Examples 55–61, siloxane-coated hollow fibers on which amine functionalities had been introduced prepared in accordance with the procedures of Examples 2–4 and 9–12, are reacted with a PEO solution according to the procedures set forth in Example 47.

Upon analysis, it is determined that 40–55% of the carbon atoms on the surface are attributed to PEO coupling to the siloxane surface of the siloxane-coated hollow fibers.

EXAMPLES 62–66

In Examples 62–66, a siloxane-coated polymeric substrate onto which amine functionalities have been incorporated according to the procedures set forth in Examples 5–8 and 14, respectively, are reacted with the PEO solution described in, according to the procedures of, Example 46.

Upon analysis, it is determined that 40–55% of the carbon atoms on the surface are attributed to PEO coupling to the siloxane surface of the siloxane-coated substrate.

EXAMPLES 67–71

In Examples 67–71, a siloxane-coated polymeric substrate into which amine functionalities have been incorporated according to the procedures set forth in Examples 5–8 and 14, respectively, are reacted with the PEO solution described in, according to the procedures of, Example 47.

Upon analysis, it is determined that 40–55% of the carbon atoms on the surface are attributed to PEO attachment to the siloxane surface of the siloxane-coated substrate.

5. PEO Reaction With Bioactive Molecules

According to the present invention, the unbound end of the PEO is reacted with bioactive molecules to covalently bond those bioactive molecules to the PEO which is itself bonded to the polymer surface. An important preferred embodiment of the present invention is to bind a plurality of different bioactive molecules to the PEO linkages in order to result in a polymer surface having multifunctional thrombo-resistant properties.

Such bonding of a plurality of bioactive molecules to the PEO on the siloxane surface of a blood gas exchange device occurs when the device is placed in a solution containing a variety of bioactive molecules (referred to generically as a "PIE" solution; "PIE" is an acronym for Prosthetic Intimal Endothelium). One preferred formulation of a PIE solution within the scope of the present invention is set forth in Table III.

TABLE III

| | |
|---|---|
| Heparin (80,000 USP units) | 570 mg |
| Urokinase powder (5% in formulation) | 15 mg |
| Ticlopidine | 80 mg |
| Plasmin Powder (activity 3–6 units/mg) | 15 mg |
| Tissue Plasminogen Activator (TPA) | 15 mg |
| Prostaglandin $E_1$ | 1 mg |

The PIE solution is prepared by dissolving heparin in 100 ml phosphate buffered saline (having a pH in the range of from about 7.1 to about 7.5 (preferably a pH of about 7.4) resulting in a concentration in the range from about to about 1500 USP units per milliliter. Preferably, the heparin concentration is about 1000 USP units per milliliter. The remaining bioactives are added to the heparin solution in the amounts indicated in Table II.

The PEO/siloxane surface is soaked in the PIE solution for about 12 hours without agitation. The PIE solution is maintained at ambient temperature in the range from about 20° C. to about 30° C. Upon removal from the solution, the surface is washed with purified water, air dried, and sterilized with ethylene oxide.

It has been found than the bioactive molecules are coupled to the epoxide groups of the PEO chains through any primary amines available on the bioactive molecule. While the exact mechanism is not known, it is theorized that the heparin, urokinase, plasmin, and TPA are coupled to the PEO as shown below.

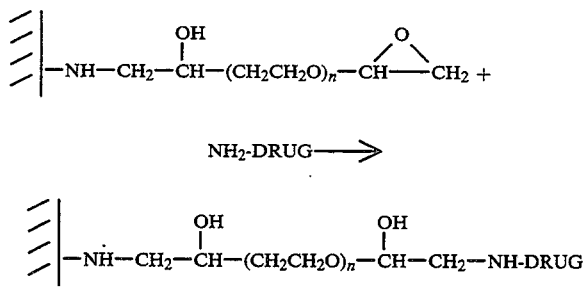

NH$_2$-DRUG $\longrightarrow$

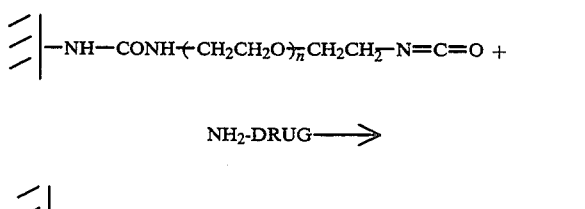

"NH$_2$-DRUG" refers to an amine-containing bioactive molecule. The bioactive molecules are coupled to isocyanate-terminated PEO chains through a similar mechanism shown below.

—NH—CONH$+$CH$_2$CH$_2$O$)_{\overline{n}}$CH$_2$CH$_2$—N=C=O +

NH$_2$-DRUG $\longrightarrow$

—NH—CONH$+$CH$_2$CH$_2$O$)_{\overline{n}}$CH$_2$CH$_2$—NHCO—NH-DRUG

D. Exemplary Embodiment of the Present Invention

Further typical examples illustrating the method of preparing thrombo-resistant compositions within the scope of the present invention are given hereinbelow. These examples, as well as Examples 1–71, should be considered be only illustrative of the present invention and not a complete identification of all embodiments of the present invention.

EXAMPLE 72

In Example 72, siloxane-coated hollow fibers onto which PEO chains have been introduced in accordance with the procedures of Examples 19, were reacted with a PIE solution containing various bioactive molecules.

The PIE solution was prepared by obtaining eight (8) 10-ml vials of heparin dissolved in phosphate buffered saline (pH 7.4) having a concentration of 1000 USP units/ml. Suitable heparin was obtained from Diosynth, Sigma, Organon, and Calbiocnem. Other bioactive molecules were then dissolved into the heparin solution as
- 15 mg urokinase powder (Sigma), 5% in formulation:
- 80 mg ticiopidine (Syntex); and
- 15 mg plasmin power (Sigma), with an activity from 3–6 units/mg.

Additional phosphate buffered saline (pH 7.4) was added to give a total volume of 100 ml.

The PEO containing hollow fibers were immersed in the PIE solution for at least twelve (12) hours without agitation. The PIE solution was maintained at ambient temperature in the range from about 20° C. to about 30° C. Upon removal from the PIE solution, the hollow fibers were rinsed ten (10) times with 100 ml of purified water to remove any unbound bioactive molecules. The hollow fibers were air dried and sterilized with ethylene oxide.

The surfaces were analyzed by ESCA and found to contain nitrogen and sulfur containing compounds. Analysis with trinitrobenzene sulfonic acid (TNBS) (an analytical technique for proteins) demonstrated measurable quantities of proteins on the surface (urokinase, plasmin, and TPA). Analysis using a solution depletion method with toluidine blue indicated heparin to be present in amounts similar or greater than those of other heparin-bound preparations reported in the literature.

Thrombogencity tests were performed utilizing the procedures described in Mortensen et al., "A Practical Screening Test for Thrombogenicity of Intraarterial Catheters—Preliminary Report," *Artificial Organs*, Vol. 2, Supp., pp. 76–80, 1978, which is incorporated herein by reference. Thrombogenicity testing results have indicated that the bioactive molecules are present and active on the surface. Small bundles of treated hollow fibers were implanted into the carotid and femoral arteries of large dogs for a period of 30 minutes. The amount of adherent thrombus and that expelled from the artery following withdrawal of the bundle was weighed and found to be significantly less than that of the controls.

EXAMPLES 73

In Example 73, multifunctional thrombo-resistant hollow fibers were prepared in accordance with the procedure of Example 70, except that after the hollow fibers were removed from the PIE solution and rinsed with purified water, the hollow fibers were soaked in a one percent (1%) glutaraldehyde solution in a pH 7.4 phosphate buffer for one (1) hour. After removal from the glutaraldehyde solution, the hollow fibers were rinsed ten (10) times with 100 ml of a pH 7.4 phosphate buffer solution. The hollow fibers were then soaked in a 0.13 M glycine solution in a pH 7.4 phosphate buffer for 72 hours. Upon removal from the glycine solution, the hollow fibers were rinsed ten (10) times with 100 mi of purified water. The hollow fibers were air dried and sterilized with ethylene oxide.

The additional glutaraldehyde and glycine treatments increased the cross-linking of molecules on the substrate surface thereby enhancing the stability of the bioactive molecules. The surfaces were analyzed by ESCA according to the procedures of Example 72 and demonstrated measurable II quantities of proteins and heparin on the surface.

Thrombogenecity testing according to the procedures given in detail in Example 72 have indicated that the bioactive molecules are present and active on the surface. No significant differences were noted between the fibers prepared according to the procedures of Example 72.

EXAMPLES 74–75

In Examples 74–75, siloxane-coated hollow fibers onto which PEO chains had been introduced in accordance with the procedures of Examples 19 and 21, respectively, were reacted with the PIE solution according to the procedures set forth in Example 70 except that the PIE solution contained the following bioactive substances in the indicated quantities: heparin (570 mg), urokinase (15 mg) and prostaglandin $E_1$ (1 mg).

The surfaces were analyzed according to the procedures described in Example 72 and demonstrated measurable quantities of proteins and heparin on the surface.

Thrombogenecity testing according to the procedures described in detail in Example 72 have indicated that the bioactive molecules are present and active on the surface. The thrombogenecity index of these samples were only slightly less than those of the samples prepared according to the procedures of Example 72.

EXAMPLES 76-77

In Examples 76-77, siloxane-coated hollow fibers onto which PEO chains had been introduced in accordance with the procedures of Examples 19 and 21, respectively, are reacted with the PIE solution according to the procedures set forth in Example 72 except that the PIE solution contains the following bioactive substances in the indicated proportions: heparin, 570 mg; streptokinase, 15 mg; aspirin, 80 mg; and sulfinpyrazone, 30 mg.

Thrombogenecity testing of these PIE coupled surfaces indicate that the bioactive molecules are present and active on the surface. The thrombogenecity index of the samples are slightly less than those of the samples prepared according to the procedures of Examples 72 and 74.

EXAMPLE 78

Amine containing siloxane-coated hollow fibers prepared substantially in accordance with the procedures of Example 1 were placed in a PIE solution containing various hisactive molecules. The PIE solution was prepared according to the procedure described in Example 72.

The amine-containing hollow fibers were immersed in the PIE solution for at least twelve (12) hours without agitation. The PIE solution was maintained at ambient temperature in the range from about 20° C. to about 30° C. Upon removal from the PIE solution, the hollow fibers were rinsed ten times with 100 ml of purified water. The hollow fibers were air dried and sterilized with ethylene oxide.

The thrombogenecity tests indicated that the bioactives were present and active, even in the absence of PEO. ESCA, toluidine blue, and TNBS analysis indicated that an increased amount of the bioactives were coupled onto the surface. However, the higher amount of bioactives did not translate into greater biological activity.

EXAMPLES 79-80

In Examples 79-80, siloxane-coated hollow fibers onto which PEO chains had been introduced in accordance with the procedures of Examples 19 and 21, respectively, are reacted with the PIE solution according to the procedures set forth in Example 71, except that the PIE solution contains the following bioactive substances in the indicated proportions:

| | |
|---|---|
| Heparin (80,000 USP units) | 570 mg |
| Urokinase powder (Sigma, 5% in formulation) | 15 mg |
| Ticlopidine (Syntex) | 80 mg |
| Plasmin Powder (Sigma, activity 3-6 units/mg) | 15 mg |
| Tissue Plasminogen Activator (TPA) | 15 mg |
| Prostaglandin E$_1$ | 1 mg |

Thrombogenicity testing of these PIE coupled surfaces indicate that the bioactive molecules are present and active on the surface. The thrombogenicity index of the samples are slightly greater than those of the samples prepared according the procedures of Examples 74 and 75.

Other drugs, not listed in Table II, are possible candidates for immobilization within the scope of the present invention. For example, drugs which have been used to passivate platelets include the following: sulfin-pyrazone (a prodrug), iloprost (a synthetic prostacyclin analogue) dipyramidole, aspirin, U-63557A, APS-306, and Prostacyclin (PGI$_2$). Complement inhibitor candidates include the following drugs: FUT-175 (Nafamstet Mesilate), and p-Guanindinobenzate derivatives, and Chloroquine. Potential protein lysers (Fibrinoiytics) include the following drugs: Streptokinase and AP-SAC. Finally, MD-805 is a known thrombin inhibitor. Many of these drugs are unsuitable for permanent covalent attachment due to their mechanism of action. However, if they were bound by a cleavable bond such as an amide bond, they could be released for local administration.

The drugs which are not suitable for the current preferred embodiment within the scope of the present invention include: sulfinpyrazone which must be metabolized before it is active; dipyramidole, which must enter into a platelet to be effective; and aspirin, which acetylates all other proteins and inactivates them.

Many of the foregoing drugs are still experimental and have not yet received Food and Drug Administration (FDA) approval for human use in the United States. Nevertheless, these drugs are given to illustrate the type of drugs which may be suitable for use within the scope of the present invention.

E. Summary

Although the above discussion has described a multifunctional thrombo-resistant coating for use with blood gas exchange devices, it will be appreciated that the thrombo-resistant coating may be adapted for use with other blood-contacting surfaces. Moreover, the principles described within the scope of the present invention may be used in connection with surfaces which initiate reactions similar to the blood-material incompatibility reactions. For instance, the principle of protein resistant surfaces achieved by terminally grafting PEO to the surface may be applied to contact lenses which are susceptible to protein deposit buildup. Other principles within the scope of this invention include the use of PEO coupled antibodies on chromatography supports. The PEO minimizes the nonspecific binding of protein while the bioactive antibodies are active and capable of specifically isolating other molecules.

In summary, the multifunctional thrombo-resistant compositions and methods disclosed herein represent a significant departure from traditional thrombo-resistant coating techniques. The present invention counteracts a wide range of blood-material incompatibility reactions without inhibiting the gas permeability of the blood-contacting surface. This is accomplished by immobilizing various bioactive molecules which counteract blood material incompatibility reactions to the blood-contacting surface through individual poly(ethylene oxide) spacer chains. Because the bioactive molecules are tethered away from the blood-contacting surface, the molecules avoid problems of steric hindrance and possess an activity approaching she activity in solution. In addition, the bioactive molecules are covalently bound to the blood-contacting surface, thereby eliminating leaching of the bioactive molecules into the blood plasma and prolonging the effectiveness of the thrombo-resistant composition.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A gas permeable membrane for effecting extrapulmonary blood gas exchange, the membrane comprising a gas permeable substrate which is coated with a polyfunctional thrombo-resistant composition comprising a siloxane surface which is permeable to a gas onto which a plurality of at least two different bioactive molecules are covalently bonded, the at least two different bioactive molecules being covalently bonded to the siloxane surface and away from the siloxane surface through a plurality of poly(ethylene oxide) chains without precluding the gas permeability of the substrate, said bioactive molecules being capable of counteracting specific blood-material incompatibility reactions.

2. A gas permeable membrane for effecting extrapulmonary blood gas exchange as defined in claim 1, wherein the poly(ethylene oxide) chains comprises poly(ethylene oxide) bis (glycidyl ether).

3. A gas permeable membrane for effecting extrapulmonary blood gas exchange as defined in claim 1, wherein the poly(ethylene oxide) chains comprises poly(ethylene oxide) bis(isocyanate).

4. A gas permeable membrane for effecting extrapulmonary blood gas exchange as defined in claim 1, wherein the plurality of at least two different bioactive molecules is selected from the group consisting of heparin, urokinase, plasmin, and ticiopidine.

5. A gas permeable membrane for effecting extrapulmonary blood gas exchange as defined in claim 1, wherein the plurality of at least two different bioactive molecules is selected from the group consisting of heparin, urokinase, TPA, and prostaglandin $E_l$.

6. A gas permeable membrane for effecting extrapulmonary blood gas exchange as defined in claim 1, wherein the plurality of at least two different bioactive molecules is selected form the group consisting of heparin, urokinase, TPA, plasmin, prostaglandin $E_1$, and ticiopidine.

* * * * *

UNITED STATES PATENT AND TRADEMARK OFFICE
CERTIFICATE OF CORRECTION

PATENT NO. : 5,342,693

DATED : August 30, 1994

INVENTOR(S) : SUZANNE WINTERS et al.

It is certified that error appears in the above-identified patent and that said Letters Patent is hereby corrected as shown below:

```
Column 2, line 5, "warlatin" should be --warfarin--
Column 4, lines 14-15, "ticiopidine" should be --ticlopidine--
Column 8, lines 22-23, "miasma-coated" should be --plasma-coated--
Column 8, line 25, "no" should be --to--
Column 9, line 58, "," should be --.--
Column 9, line 58, "gibers" should be --fibers--
Column 9, line 59, "," should be --.--
Column 9, line 60, "," should be --.--
Column 10, line 12, delete "a"
Column 10, line 21, "into" should be --onto--
Column 10, line 26, "were" should be --was--
Column 10, line 33, "wants" should be --watts--
Column 10, line 45, "she" should be --the--
Column 10, line 53, after "onto" insert --the--
Column 12, line 13, "no" should be --to--
Column 13, line 10, "hexamethyicyclotrisiloxane" should be
--hexamethylcyclotrisiloxane--
Column 13, line 26, "The" should be --the--
Column 13, line 34, "toe" should be --not--
Column 14, line 4, "presumably" should be --Presumably--
Column 14, line 15, "Example ! 0" should be --Example 10--
Column 14, line 50, after "150" insert --watts--
Column 15, line 25, "see" should be --set--
Column 15, line 44, delete "25"
Column 16, line 39, "mends" should be --tends--
Column 18, line 4, delete "1.5"
Column 20, line 1, "Indicated" should be --indicated--
Column 20, line 32, delete "lo"
Column 20, line 51, after "set forth" insert --in--
Column 20, line 58, "in" should be --In--
Column 22, line 51, after "about" insert --500--
```

UNITED STATES PATENT AND TRADEMARK OFFICE
CERTIFICATE OF CORRECTION

PATENT NO. : 5,342,693
DATED : August 30, 1994
INVENTOR(S) : SUZANNE WINTERS et al.

It is certified that error appears in the above-identified patent and that said Letters Patent is hereby corrected as shown below:

```
Column 23, line 36, after "considered" insert --to--
Column 23, line 48, "units/mi." should be --units/ml.--
Column 23, line 49, "Calbiocnem" should be --Calbiochem--
Column 23, line 52, "ticiopidine" should be --ticlopidine--
Column 24, line 35, "mi" should be --ml--
Column 24, line 43, delete "ll"
Column 25, line 25, "hisactive" should be --bioactive--
Column 26, line 7, "(Fibrinoiytics)" should be --(Fibrinolytics)--
Column 26, line 59, "she" should be --the--
Column 28, lines 11 and 22, "ticiopidine" should be --ticlopidine--
```

Signed and Sealed this

Twenty-eight Day of March, 1995

*Attest:*

BRUCE LEHMAN

*Attesting Officer*     *Commissioner of Patents and Trademarks*